United States Patent [19]

Patel et al.

[11] Patent Number: 5,559,017

[45] Date of Patent: Sep. 24, 1996

[54] MICROBIAL REDUCTION OF BENZAZEPINES AND BENZOTHIAZEPINE DERIVATIVES

[75] Inventors: Ramesh N. Patel, Bridgewater; Laszlo J. Szarka, East Brunswick; Richard H. Mueller, Ringoes, all of N.J.

[73] Assignee: E. R. Squibb & Sons, Inc., Princeton, N.J.

[21] Appl. No.: 615,736

[22] Filed: Nov. 19, 1990

Related U.S. Application Data

[63] Continuation-in-part of Ser. No. 391,019, Aug. 9, 1989, abandoned.

[51] Int. Cl.$^6$ .......................... C12P 17/14; C12P 17/10; C12P 17/16
[52] U.S. Cl. .......................... 435/120; 435/118; 435/121; 435/122; 435/280; 435/822; 435/911
[58] Field of Search .................... 435/117, 118, 435/119, 120, 121, 122, 190, 280, 822, 911

[56] References Cited

U.S. PATENT DOCUMENTS

| | | | |
|---|---|---|---|
| 3,806,418 | 4/1974 | Yamamoto et al. | 435/121 |
| 4,584,131 | 4/1986 | Floyd et al. | 260/239 |
| 4,694,002 | 9/1987 | Floyd et al. | 514/211 |
| 4,748,239 | 5/1988 | Floyd et al. | 540/523 |
| 4,752,645 | 6/1988 | Das et al. | 540/523 |
| 4,767,756 | 8/1988 | Das et al. | 514/213 |
| 4,771,047 | 9/1988 | Das | 514/213 |
| 4,774,239 | 9/1988 | Das | 514/213 |

OTHER PUBLICATIONS

Christen M, J. Chem Soc. Chem Commun, pp. 264–266 (1988).
"Guide to Making Deposits" by ATCC pp. 5–7 (1992).
"Enzyme Nomenclature" by International Union of Biochemistry pp. 7, 20–119 (1984).
Hummel, W., Appl Microbiol Biotechnol 34:15–19 (1990).
Williaert, J., Bioorganic Chem. 16:223–231 (1988).
Shen, G–J., J. Chem. Soc. Chem. Commun (9) 677–9 (1990).
Ohta, H., et al., Agriculture Biological Chemistry, vol. 51, pp. 2421–2427, 1987.
Fujisawa, T. et al., Tetrahedron Letters, vol. 26, pp. 6089–6092, 1985.

Primary Examiner—Michael G. Wityshyn
Assistant Examiner—S. Saucier
Attorney, Agent, or Firm—Timothy J. Gaul

[57] ABSTRACT

A novel process comprises reducing a benzazepine or benzothiazepine at the 3-position in d-cis configuration by treatment with reductase-supplying microorganisms or enzymes derived therefrom. The process can be catalyzed in a single stage by growing microbial cultures or in a two-stage fermentation/transformation by resting cell-suspensions. The enzymes derived from the microorganisms can be used in free state or immobilized form. The microorganisms and enzymes catalyzes the specific reduction with 90 to 99% conversion efficiency to 99% or greater optical purity of the desired enantiomer.

24 Claims, No Drawings

MICROBIAL REDUCTION OF BENZAZEPINES AND BENZOTHIAZEPINE DERIVATIVES

This is a continuation-in-part of U.S. application Ser. No. 391,019 filed Aug. 9, 1989, now abandoned.

FIELD OF THE INVENTION

This invention relates to preparation of chemical intermediates of cardiovascular agents, and in particular to intermediates of benzazepine and benzothiazepine derivatives.

BACKGROUND OF THE INVENTION

Various benzazepine and benzothiazepine derivatives display, for example, vasodilating activity. (See, e.g., U.S. Pat. Nos. 4,774,239; 4,767,756; 4,771,047; 4,694,002; 4,752,645; 4,748,239; and 4,584,131.) Useful benzazepine and benzothiazepine compounds can be described by the formula

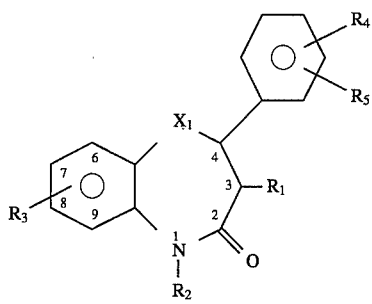

wherein, in formula I and throughout the specification, $X_1$ is —$CH_2$— or —S—;

$R_1$ is

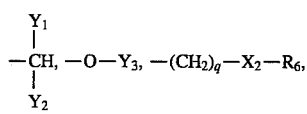

hydrogen, alkyl, acetyl, aryl, alkenyl, alkynyl, arylalkyl, —$SR_9$, —$N_3$, —$NH_2$,

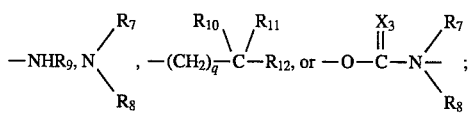

when $X_1$ is —$CH_2$—, $R_2$ is hydrogen, $$-(CH_2)_{\overline{n}}-N\begin{matrix}R_7\\R_8\end{matrix},$$

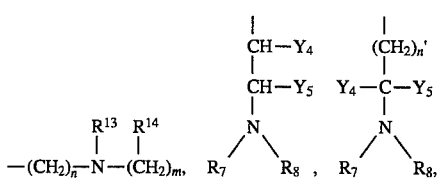

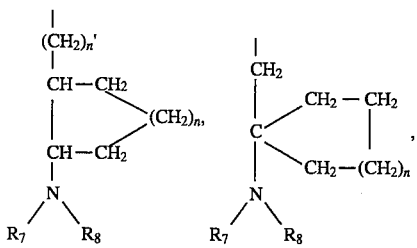

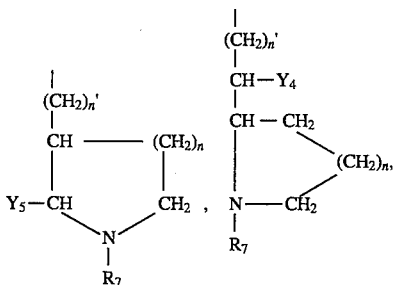

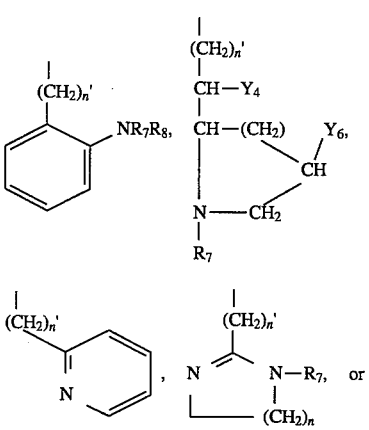

when $X_1$ is —S—, $R_2$ is hydrogen,

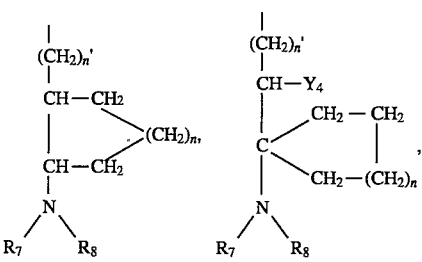

-continued

[Structure: CH(CH₂)ₙ' — (CH₂)ₙ — CH₂ connected to N–R₇, with Y₅–CH branch]

[Structure: phenyl ring with (CH₂)ₙ' substituent and NR₇R₈]

[Structure: CH(CH₂)ₙ' with CH–Y₄, CH–(CH₂)–Y₆, CH, and N–R₇ forming ring with CH₂]

[Structure: pyridine ring with (CH₂)ₙ' substituent]

[Structure: N=C((CH₂)ₙ')–N(R₇)–(CH₂)ₙ ring, or N=C((CH₂)ₙ')–N–R₇ with double bond]

$R_3$, $R_4$ and $R_5$ are each independently hydrogen, halogen, alkyl, alkoxy, aryloxy, arylalkoxy, diarylalkoxy, arylalkyl, cyano, hydroxy, alkanoyloxy, nitro, $$-O-\overset{O}{\underset{\|}{C}}-NR_7R_8,$$

fluoro-substituted alkoxy, fluro-substituted alkyl, (cycloalkyl)alkoxy, $$-NO_2, -NX_4X_5, -S-(O)_m aryl, -\overset{O}{\underset{\|}{C}}-X_6, -\overset{O}{\underset{\|}{C}}-X_7,$$

$R_6$ is hydrogen, alkyl, acetyl, aryl, arylalkyl, or —NR₇R₈;

$R_7$ and $R_8$ are each independently hydrogen, alkyl, cycloalkyl, or arylalkyl; or $R_7$ and $R_8$, together with the nitrogen atom to which they are attached, are azetidinyl, pyrrolidinyl, piperidinyl, or morpholinyl;

$R_9$ is acyl, alkyl, aryl, or arylalkyl;

$R_{10}$ and $R_{11}$ taken together are oxygen or $R_{10}$ is hydrogen and $R_{11}$ is hydroxy;

$R_{12}$ is hydrogen, hydroxy, alkyl, aryl, arylalkyl, —O—alkyl, —O—aryl, or —O—arylalkyl;

$R_{13}$ is hydrogen, alkyl, cycloalkyl, or arylalkyl;

$R_{14}$ is heterocyclo or heteroaryl;

$X_2$ is oxygen, sulfur, or a single bond when $R_6$ is —NR₇R₈;

$X_3$ is oxygen or sulfur;

$X_4$ and $X_5$ are each independently hydrogen, alkyl, alkanoyl, arylcarbonyl, heteroarylcarbonyl or —C—NR₇R₈;

$X_6$ is hydroxy, alkoxy, aryloxy, amino, alkylamino, or dialkylamino;

$X_7$ is alkyl, alkoxy, or aryloxy; but if $R_3$ is a 7-alkyl group, it must have a tertiary carbon atom bonded to the ring;

$Y_1$ and $Y_2$ are each hydrogen or alkyl; or $Y_1$ is hydrogen and $Y_2$ is alkenyl, alkynyl, aryl, heteroaryl, or cycloalkyl; or $Y_1$ and $Y_2$, together with the carbon atom to which they are attached, are cycloalkyl;

$Y_3$ is hydrogen, alkyl, alkanoyl, alkenyl, arylcarbonyl, heteroarylcarbonyl, or —C—NR₇R₈

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ is hydrogen, hydroxy, alkoxy, aryloxy, or aralkoxy;

m is 0, 1, or 2;

n or n' is 0, 1, 2, or 3; and q is an integer from 0 to 5.

Exemplary formula I compounds are

[Structure: benzazepine with CF₃ and methyl on one phenyl, 4-methoxyphenyl substituent, OC(O)CH₃ (acetate) group, N-cyclopentyl with NH]

and

[Structure: benzazepine with CF₃ and methyl on one phenyl, 4-methoxyphenyl substituent, OH group, N-cyclopentyl with NH]

Exemplary formula I compounds are also described in, for example, U.S. Pat. No. 4,902,684.

The carbon atoms in the 3- and 4-positions of the benzazepine nucleus and in the 2- and 3-positions of the benzothiazepine nucleus of formula I compounds are asymmetric carbons. The compounds of formula I, therefore, exist in enantiomeric and diastereomeric forms and as racemic mixtures thereof. All are within the scope of formula I. It is believed that formula I compounds having the d-cis configuration are the most potent and are therefore preferred.

The following definitions apply throughout this specification, unless otherwise limited in specific instances.

The terms "alkyl" and "alkoxy" refer to both straight and branched chain groups. Those groups having 1 to 10 carbon atoms are preferred.

The terms "alkenyl" and "alkynyl" refer to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino (—NH₂), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl or carboxyl groups.

The term "heteroaryl" refers to an aromatic heterocyclic group having at least one heteroatom in the ring. Preferred groups are pyridinyl, pyrrolyl, imidazolyl, furanyl, thienyl, or thiazolyl.

The term "heterocyclo" refers to fully saturated or unsaturated rings of 5 or 6 atoms containing one or two oxygen and sulfur atoms and/or one to four nitrogen atoms, provided that the total number of hetero atoms in the ring is 4 or less. The hetero ring is attached by way of an available carbon atom. The term "heterocyclo" also includes bicyclic rings wherein the five-or six-membered ring containing oxygen, sulfur, or nitrogen atoms as defined above is fused to a benzene ring and the bicyclic ring is attached by way of an available carbon atom in the benzene ring. The term "heterocyclo" further includes such monocyclic and bicyclic rings wherein an available carbon atom is substituted with:

a lower alkyl of 1 to 4 carbons;

a lower alkylthio of 1 to 4 carbons;

a lower alkoxy of 1 to 4 carbons;

a halo;

a nitro;

a keto;

a cyano;

a hydroxy;

an amino;

—NH-alkyl, wherein the alkyl is of 1 to 4 carbons;

—N(alkyl)$_2$, wherein the alkyl is of 1 to 4 carbons;

—CF$_3$;

NCS; or

OCHF$_2$.

The term "heterocyclo" further includes monocyclic and bicyclic rings wherein two or three available carbons have substituents selected from methyl, methoxy, methylthio, halo, CF$_3$, nitro, hydroxy, amino, and OCHF$_2$.

The term "cycloalkyl" refers to groups having 3, 4, 5, 6 or 7 carbon atoms.

The terms "halogen" and "halo" refer to fluorine, chlorine, bromine, iodine, and trifluoromethyl.

The terms "fluoro-substituted alkyl" and "fluoro-substituted alkoxy" refer to alkyl and alkoxy groups (as described above) in which one or more hydrogens have been replaced by fluorine atoms. Exemplary groups are trifluoromethyl, 2,2,2,-trifluoromethyl, pentafluoroethyl, fluoromethoxy, difluoromethoxy, etc.

The term "alkanoyl" refers to groups having the formula $$\text{alkyl-}\overset{\overset{\text{O}}{\|}}{\text{C}}-.$$

Those alkanoyl groups having 2 to 11 carbon atoms are preferred.

The compounds of formula I can be prepared by first reacting a 2-nitrotoluene having the formula

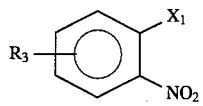

II with a benzylidine malonate having the formula

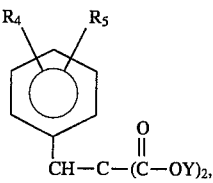

III wherein Y is alkyl. The reaction can be run in a polar nonprotic solvent (e.g., dimethylformamide), in the presence of a strong base (e.g., sodium hydride) and yields a product having the formula

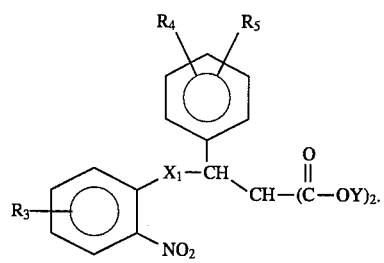

IV

Reduction of a compound of formula IV yields the corresponding compound having the formula

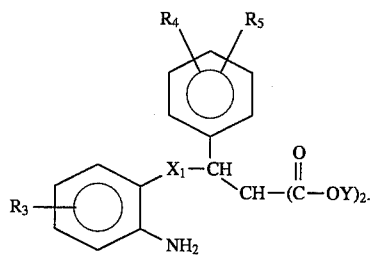

V

The reduction can be accomplished by catalytic hydrogenation (using, for example, palladium on charcoal as a catalyst) or by using a chemical reducing agent (e.g., ferrous sulfate or stannous chloride).

Treatment of an amine of formula V with an alkali metal alkoxide (e.g., sodium methoxide) and an alcohol (e.g., methanol) or with potassium hexamethyldisilazide in a solvent such as tetrahydrofuran or toluene, yields the corresponding benzazepine having the formula

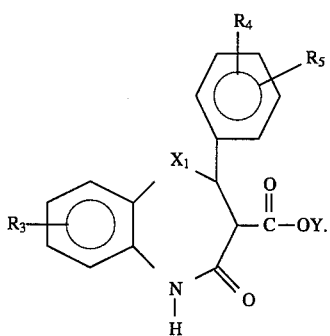

VI

Reaction of a compound of formula VI with a reducing agent, such as lithium aluminum hydride, in a solvent such as tetrahydrofuran, at low temperature yields the corresponding compound having the formula

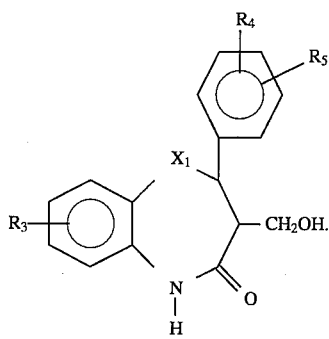
VII

Compound VII can thereafter be reacted with p-toluenesulfonylchloride or methanesulfonylchloride in the presence of a base (e.g., pyridine) to provide a compound having the formula

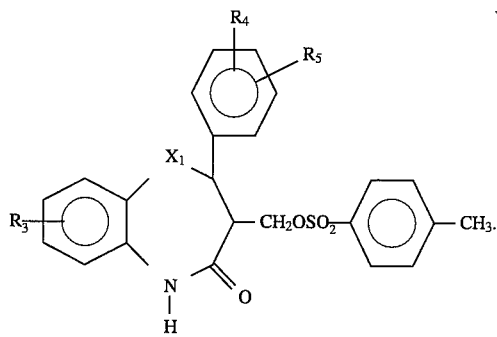
VIII

Compound VIII can be reacted with a base in the presence of a solvent (e.g., dichloromethane or dimethylformamide) at room temperature to provide the corresponding compound having the formula

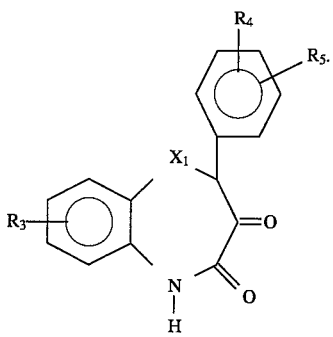
IX

Compound IX may then be treated with an alkali metal hydride (e.g., sodium hydride) in an inert solvent (e.g., dimethylsulfoxide), followed by reaction with a compound having the formula
IX'

$R_2$-halogen to form a compound having the formula

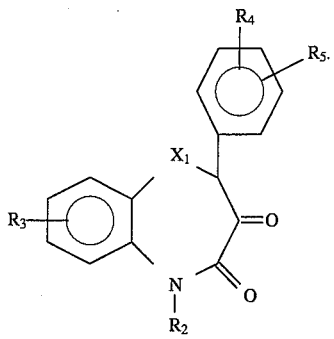
X

If compound X could be efficiently reduced at the 3-position, it could form the useful intermediate having the formula

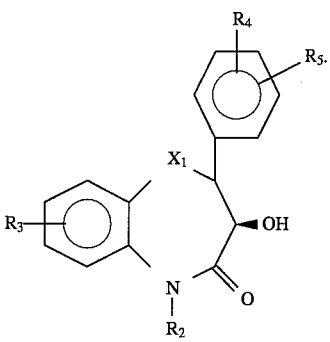
XI

In the prior art, compound XI could be formed by decarboxylation of a compound having the formula

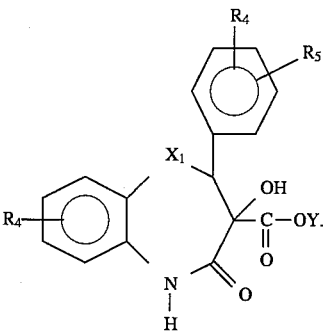
XII by treating compound XII with, for example, excess lithium iodide in hot pyridine. See U.S. Pat. No. 4,748,239. This process yields a mixture of compound XI and its isomer

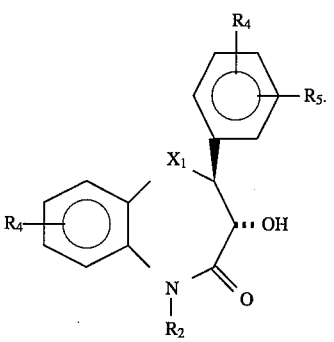
XI'

Formula I compounds can be prepared from compounds XI and XI' as described in U.S. Pat. Nos. 4,584,131; 4,748,239; 4,752,645; 4,694,002; 4,771,047; 4,767,756; and 4,774,239. Further preparation of formula I compounds is described in U.S. patent application Ser. Nos. 208,521 (filed Jun. 20, 1988); 353,806, (filed May 22, 1989), now U.S. Pat. Nos. 4,902,684; and 334,025 (filed Apr. 6, 1989). For compounds wherein $X_1$ is —S—, see U.S. Pat. Nos. 4,584, 131 and 4,694,002.

Compound XI is preferred over compound XI' because compound XI is in the more potent d-cis configuration. A process that favors production of compound XI, therefore, would be a useful addition to the art.

BRIEF DESCRIPTION OF THE INVENTION

In accordance with the present invention, a novel process for preparing formula XI compounds is disclosed. In essence, a formula X compound is treated with a microorganism comprising reductase enzyme or reductase enzyme isolated from microorganisms, yielding a corresponding formula XI compound. In a preferred embodiment of this invention, $R_2$ is hydrogen in compound X, which is first microbially or enzymatically treated in accordance with this invention and then reacted to form a compound having the $R_2$ group shown in compounds IA and IB.

The process has the advantage of producing a stereospecific result. Unlike the prior art, the process primarily yields the preferred d-cis enantiomer (compound XI) rather than a mixture of preferred and unpreferred enantiomers. Additional advantages include a single step stereospecific reduction of formula X compound to formula XI compound compared with multi-step chemical synthesis. When the transformation is catalyzed at ambient temperature and pressure, one obtains high conversion (98%) and enantiomeric purity of greater than 99% of the desired enantiomer.

DETAILED DESCRIPTION OF THE INVENTION

The process can be carried out in a single stage or two-stage fermentation and transformation. In a single stage process, microorganisms used are grown in an appropriate medium containing carbon and nitrogen sources. A compound is added to the microbial cultures and transformation of the formula X compound to the formula XI compound may be continued until complete conversion is obtained. In the two-stage process, microorganisms are grown in an appropriate medium by fermentation exhibiting the desired reductase activity in the first stage. Cells are suspended in an appropriate buffered solution to prepare cell suspensions. The formula X compound is mixed with the microbial cell suspensions, and the transformation of compound X to compound XI is catalyzed by microbial cell suspensions. The reaction may continue until nearly all of the formula X compound is transformed to formula XI compound.

A carbon source may be added during transformation. Formula X compound may be added as an inducer during growth of microorganisms. The microorganisms or microbially derived reductases may be used in free state or immobilized on support.

Typical microorganisms for this process include genera from bacteria, yeasts, and fungi. Typical genera of microorganisms include: Achromobacter, Acinetobacter, Actinomyces, Alcaligenes, Arthrobacter, Azotobacter, Bacillus, Brevibacterium, Corynebacterium, Flavobacterium, Methylomonas, Mycobacterium, Nocardia, Pseudomonas, Rhodococcus, Streptomyces, Xanthomonas, Aspergillus, Candida, Fusarium, Geotrichum, Hansenula, Kloeckera, Penicillium, Pichia, Rhizopus, Rhodotorula, Saccharomyces, Trichoderma, and Rhodopseudomonas. Preferred microorganisms include *Arthrobacter simplex, Nocardia globerula, Nocardia restricta, Nocardia salmonicolor, Rhodococcus fascians, Rhodococcus rhodochrous, Mycobacterium vacca, Nocardia mediterranei, Nocardia autotrophica, Rhodococcus equi, Arthrobacter paraffineus, Hansenula polymorpha,* and *Candida albicans.*

The inventors have also found that microorganisms can be used in free state as wet cells, freeze-dried cells or heat-dried cells. Immobilized cells on support by physical adsorption or entrapment can also be used for this process.

Culture media provide nutrients necessary for the growth of the microbial cells. A typical medium for growth includes necessary carbon sources, nitrogen sources, and trace elements.

Carbon sources include sugars such as maltose, lactose, glucose, fructose, glycerol, sorbitol, sucrose, starch, mannitol, and the like; organic acids such as sodium acetate, sodium citrate, and the like; amino acids such as sodium glutamate and the like; alcohols such as ethanol, propanol, and the like.

Nitrogen sources include N-Z Amine A, corn steep liquor, soy bean meal, beef extracts, molasses, baker's yeast, tryptone, nutrisoy, sodium nitrate, ammonium sulfate, and the like.

Trace elements include phosphates and magnesium, manganese, calcium, cobalt, nickel, iron, sodium, and potassium salts.

Typical preferred media are as follows:

| Medium 1: | | |
|---|---|---|
| Salt A Solution: | $K_2HPO_4$ | 10 grams |
| | $KH_2PO_4$ | 10 grams |
| | 100 ml distilled water. | |
| Salt B Solution: | $MgSO_4.7 H_2O$ | 4 grams |
| | NaCl | 0.2 grams |
| | $FeSO_4.7 H_2O$ | 0.2 grams |
| | $MnSO_4.5 H_2O$ | 0.2 grams |
| | 100 ml distilled water | |
| Composition: | Glucose | 15 grams |
| | $(NH_4)_2SO_4$ | 10 grams |
| | Yeast extracts | 10 grams |
| | N—Z Amine A | 10 grams |
| | $CaCO_3$ | 5 grams |
| | Salt A solution | 5 ml |
| | Salt B solution | 5 ml |
| | Tap water | 1 liter volume |
| Medium 2: | | |
| Composition: | Glucose | 20 grams |
| | Yeast extracts | 10 grams |
| | Malt extracts | 10 grams |
| | Peptone | 1 gram |
| | Tap water | 1 liter |

The efficiency of the process is affected by both the initial amount of substrate used and by the timing and amount of substrate added during the process. Substrate can be added batchwise every 1 to 12 hours or continuously during the transformation process by growing cells in a one-stage fermentation or by cell-suspensions of microorganisms as in two-stage fermentation/transformation process.

The pH of the medium may be maintained between 4.0 and 9.0, preferably between 6.0 and 8.0, during growth of microorganisms and during the transformation process.

Buffers such as tris-HCl, phosphates, sodium acetate and the like may be used to prepare suspensions of microbial cells to conduct the transformation process.

The temperature of the reaction mixture measures the heat energy available for the transformation process. Maintenance of the reaction temperature ensures that there is sufficient energy available for the process. A temperature range from about 15° C. to 60° C., preferably from about 35° C. to 50° C., is most suitable for the transformation.

The agitation and aeration of the reaction mixture affects the amount of oxygen available during the transformation process in shake-flask cultures or fermenter tanks during growth of microorganisms in a single stage or two-stage process. The agitation range from 50 to 1000 RPM is preferable, but 50 to 500 RPM is most preferred. Aeration of about 1 to 5 volumes of air per volume of media per minute (i.e., 1 to 5 v/vt) is preferred.

The optimum reaction time for the transformation process ranges from 12 to 168 hours, preferably 48 to 96 hours, measured from the time of initially treating the substrate (formula X compound) with the microorganism to achieve complete conversion of formula X compound to formula XI compound.

The transformation of compound X to compound XI may also be accomplished by reductase isolated from microorganisms. An exemplary procedure for isolating a reductase from microorganisms is described in Example 1, methods III and IV.

When $X_1$ is —$CH_2$— in compounds X and XI, compound XI may be reacted with a compound of the formula

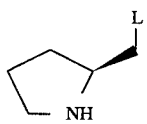

XIII (wherein L is a leaving group, such as halogen or tosyloxy, preferably tosyloxy) to provide compound I wherein $R_2$ is

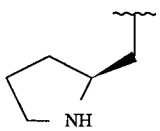

(e.g., compound IB). Compound I or XI may also be acylated by conventional techniques to provide compound I wherein $R_1$ is

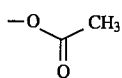

(e.g. compound IA).

The process will now be described by the following working examples. These examples demonstrate practice of the process and provide supporting data. These examples are illustrative rather than limiting. Unless otherwise indicated, all temperatures are in degrees Celsius.

EXAMPLE 1

3R-cis)-1,3,4,5-Tetrahydro-3-hydroxy-4-(4-methoxyphenyl)-6-(trifluoromethyl)-2H-1-benzazepin-2-one The substrate for this process is 4,5-dihydro-4-(4-methoxyphenyl)-6-(trifluoromethyl)-1H-1-benzazepine-2,3-dione. The structural formula of this substrate is:

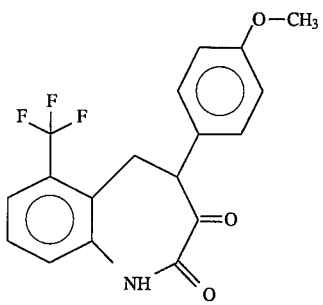

The structural formula of the desired product is:

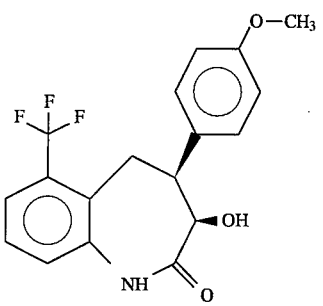

Method I

Bacterial cultures *Pseudomonas aeuriginosa* A.T.C.C. 25619, *Pseudomonas putida* A.T.C.C. 23973, *Acinetobacter calcoaceticus* A.T.C.C. 33305, *Alcaligenes euntrophus* A.T.C.C. 17697, *Mycobacterium vacca* A.T.C.C. 29678, *Rhodococcus fascians*, A.T.C.C. 12975 (*Nocardia salmonicolor* SC 6310), *Rhodococcus rhodochrous* A.T.C.C. 29670, 15906, 14349, 13808, 12975, 999, 15592, 29675, 21243, and 19150 were used. Yeast cultures *Hansenula polymorpha* A.T.C.C. 26012, *Saccharomyces cerevisiae* A.T.C.C. 12341, *Pichia pastoris* A.T.C.C. 28485, *Candida rugosa* A.T.C.C. 10571 and *Candida utilis* A.T.C.C. 26387 were used to conduct transformation of substrate to desired product.

Microorganisms were maintained in vials in liquid nitrogen. For routine development of inoculum, one vial was inoculated into 100 ml of medium 1 or medium 2 in 500-ml flasks and incubated at 28° C. to 30° C. and 250 to 300 RPM on a shaker for 24 to 48 hours. After growth of microorganisms, 10 ml of cultures were inoculated into 500-ml flasks containing 100 ml medium and incubated at 28° C. to 30° C. and 250 to 300 RPM on a shaker.

Various microorganisms (table 1) were grown in medium 1 for 48 to 72 hours at 28° C. to 30° C. and 250 to 300 RPM (resolution per minute) on a shaker. Cells were harvested and suspended in 0.2 M tris-HCl buffer pH 6.8. 10% w/v wet cell-suspensions were prepared. Cell-suspensions were supplemented with 200 μgm/ml of substrate and the transformations were conducted at 30° C., 250 RPM for 24 hours. Samples were taken and extracted five times with ethyl acetate. The ethyl acetate layers were collected after centrifugation and evaporated under nitrogen. The dried residue was dissolved in methanol and analyzed by high pressure liquid chromatography (HPLC) for identification of the substrate and the product. The chromatographic conditions were as follows:

Column: Whatman

Partisil 5-ODS-3

Mobile Phase: 45% of 0.05 M sodium acetate buffer containing 0.3 mM Na$_2$EDTA.2H$_2$O, 35% acetonitrile, 20% methanol (adjusted to pH 5.0 with acetic acid)

Flow Rate: 1 ml/min

Detector: Diode array (Hewlett Packard 1090) 240 nm

Two enantiomers were separated by HPLC analysis on Bakerbond® Chiral phase DNBPG (Baker Chemical Co., Phillipsburg, N.J.) with the following conditions:

Mobile Phase: 10/90, 2-propanol/hexane

Flow Rate: 2 ml/min.

Pressure: 30 atmosphere

Detection: 254 nm

Injection Volume: 10 μl

The desired product (structural formula XIA) was identified by the above chiral HPLC.

Two enantiomers were also separated by HPLC analysis on Bakerbond® Chiralcel OD column (Baker Chemical Co., Phillipsburg, N.J.) with the following conditions:

Mobile Phase: 10/90, 2-propanol/hexane

Flow Rate: 1 ml/min.

Pressure: 30 atmosphere

Detection: 230 nm

Injection Volume: 10 μl

The mobile phase was continuously stirred during chromatography.

Results of our analysis demonstrated that all organisms converted substrate to desired product. *Rhodococcus fascians* A.T.C.C. 12975 (*Nocardia salmonicolor* SC 6310) gave best conversion (97%) of substrate to desired products (Table 1).

TABLE 1[a]

| Microorganisms | Product (compound XIA, μgm/ml) | Conversion (%) |
|---|---|---|
| *Pseudomonas aeroginosa* ATCC 25619 | 4 | 2 |
| *Pseudomonas putida* ATCC 23973 | 5 | 2.5 |
| *Pseudomonas oleovorans* ATCC 29347 | 4.5 | 2.25 |
| *Acinetobacter calcoaceticus* ATCC 33305 | 6 | 3 |
| *Arthrobacter simplex* ATCC 6949 | 156 | 78 |
| *Rhodococcus fascians* ATCC 12975 (*Nocardia salmonicolor* SC 6310) | 194 | 97 |
| *Alkaligenes eutrophus* ATCC 17697 | 80 | 40 |
| *Mycobacterium vacca* ATCC 29678 | 176 | 88 |
| *Rhodococcus rhodochrous* ATCC 29670 | 134 | 67 |
| *Rhodococcus rhodochrous* ATCC 15592 | 128 | 64 |
| *Rhodococcus rhodochrous* ATCC 15906 | 22 | 11 |
| *Rhodococcus rhodochrous* ATCC 14349 | 30 | 15 |
| *Rhodococcus rhodochrous* ATCC 13808 | 89 | 44.5 |
| *Rhodococcus rhodochrous* ATCC 999 | 69 | 34.5 |
| *Rhodococcus rhodochrous* ATCC 29675 | 49 | 24.5 |
| *Rhodococcus rhodochrous* ATCC 21243 | 58 | 29 |
| *Rhodococcus rhodochrous* ATCC 19150 | 17 | 8.5 |
| *Hansenula polymorpha* ATCC 26012 | 65 | 32.5 |
| *Saccharomyces cerevisiae* ATCC 12341 | 55 | 27.5 |
| *Pichia pastoris* ATCC 28485 | 40 | 20 |
| *Candida rugosa* ATCC 10571 | 25 | 12.5 |
| *Candida utilis* ATCC 26387 | 67 | 33.5 |

[a]"ATCC" refers to the American Type Culture Collection.
"SC" refers to the culture collection of E. R. Squibb & Sons, Inc.

Method II

The substrate and product for Method II are the same as in Method I.

Growth of *Rhodococcus fascians* ATCC 12975 (*Nocardia salmonicolor* SC 6310) in 380-liter fermentor The growth of *Rhodococcus fascians* ATCC 12975 (*Nocardia salmonicolor* SC 6310) were conducted in 380-liter fermentors containing medium 1 or medium 2 at 28° C., 250 RPM. After 22 hours during growth phase, the substrate from Example 1 (5.0 grams in 110 ml of dimethylformamide) was added and growth was continued. The pH of the medium was maintained between 6.8 and 7.0 during further growth. Cells were harvested at log 44 hours and, after centrifugation, cell pastes were collected from various batches. Cells were stored at 4° C. or −20° C. until further use. Portions of cell samples were also heat-dried at 35° C. under vacuum.

Transformation of Substrate to Product

Shake-Flask Cultures Transformation

Cells from the above batches were suspended in 0.2 M Tris-hydrochloric acid (Tris HCl) buffer pH 7.2 at 5 to 20% w/v wet cell concentration. The transformation was conducted at 28° C., 37° C., and 45° C. on a shaker at 250 RPM. Reactor volumes were 100 ml in 500-ml flasks or 50 ml in 250-ml flasks. Periodically, samples were extracted with 2 to 5 volumes of ethylacetate and analyzed by HPLC assay for the transformation to the desired product (Table 2). Increasing temperature gave higher conversion efficiency.

Transformation in 38-liter Fermentors

Cells from the above batches were also used to conduct the transformation in 380-liter fermentors with 10% to 20% w/v cell concentration. Transformations were conducted at 25° C. in 0.1 M Tris-HCl buffer, pH 7.2 at 125 to 250 RPM. The substrate (6.25 grams in 30 ml of dimethylformamide) was added to 25 liter cell suspensions with continuous agitation and aeration. The pH was maintained between 6.5 and 7.5 during transformation. Periodically, samples were extracted with ethylacetate and analyzed by the HPLC system. Results are as shown in Table 3.

TABLE 2

Transformation by cell suspensions
*Rhodococcus fascians* ATCC 12975
(*Nocardia salmonicolor* SC 6310)

| Temperature, °C. | Product (compound XIA μgm/ml) | Percentage of Transformation |
|---|---|---|
| 28 | 694 | 53 |
| 37 | 1181 | 91 |
| 45 | 1266 | 97 |

(a) Cells were grown on medium 1 or medium 2 for 24 hours. Substrate (compound XA, 100 μgm/ml) was added at log 24 hours, and cells were harvested at log 48 hours. Cell paste was suspended in 600 ml of 0.1M Tris-HCl, pH 7.2. A 10% w/v, wet weight cells concentrations were prepared and used for transformation in 100 ml reactor volume contained in 500-ml flasks at 250 r.p.m. on shaker. Initial substrate concentration was 1300 μgm/ml.

TABLE 3

Transformation of Substrate to Product in 25 Liter Cell Suspensions of *Rhodococcus fascians* ATCC 12975 (*Nocardia salmonicolor* SC 6310) [(a)]

| Reaction Time (Hour) | Substrate (compound XA, μgm/ml) | Product (compound XIA, μgm/ml) | % Transformation |
|---|---|---|---|
| 0 (Cell Suspension) | 22 | 40 | |
| 0 (Cell Suspension + Substrate) | 200 | 41 | |
| 15 | 225 | 125 | |

TABLE 3-continued

Transformation of Substrate to Product in 25 Liter Cell
Suspensions of *Rhodococcus fascians* ATCC 12975
(*Nocardia salmonicolor* SC 6310) [a]

| Reaction Time (Hour) | Substrate (compound XA, μgm/ml) | Product (compound XIA, μgm/ml) | % Transformation |
|---|---|---|---|
| 39 | 120 | 190 | |
| 63 | 84 | 226 | |
| 91 | 15 | 310 | 99 |
| 115 | 5 | 301 | |

[a] Transformation was conducted in 380-liter fermentors containing 25 liters of cell suspensions (17% w/v, wet weight cells) in 0.1M Tris-HCl buffer, pH 7.2, at 25° C. The substrate (compound XA, 6.25 grams in 30 ml of dimethylformamide) was supplied at concentration of 250 μgm/ml.

At harvest, about 21 liters of cell-suspensions were extracted with 5 volumes of ethylacetate. The ethylacetate concentrate in a typical batch contained 5.99 grams of product (Table 4) which was further purified and characterized by Ms, CD, and HPLC System to determine enantiomeric purity of the compound. The isolated product and standard product samples were analyzed by Mass Spectroscopy. The MS analysis confirmed that the isolated product is the same as the standard compound.

TABLE 4

Recovery of the Desired Product [a]

| | Harvest | | Ethyl acetate | |
|---|---|---|---|---|
| Batch | Reaction Time (Hour) | Volume Liter | Concentrate Compound XIA (Grams) | Optical Purity (%) |
| XP 0221 | 115 | 21 | 5.99 | 99.7 |

[a] Tranformation was conducted as described in the Table 2 in a 380-liter fermentor. At harvest, 21 liters of cell-suspensions extracted with 5 volumes of ethyl acetate and ethyl acetate concentrate was analyzed for desired product recovery.

The absolute configuration of isolated product was assigned by CD analysis and HPLC analysis on chiral column which separated the two enantiomers. The CD spectra of two enantiomers indicated mirror images of each other. The biologically isolated product gave CD spectra identical to that of the desired enantiomer product. A positive CD at 258 nm signified the carbon-3 atom to be of the (R)-configuration; the negative CD at 258 nm signified the carbon-3 atom to be of the (S)-configuration. In contrast, the positive CD in the 275/280 nm system signified the carbon-4 atom to be of the (S)-configuration and negative CD in the 275/280 nm system to be of the (R)-configuration.

Finally, the analysis of the standard product and the isolated product by an HPLC analysis on chiral column confirmed that the microbially produced product is indeed the desired enantiomer in greater than 99% optical purity. The recovered product from enzymatic transformation gave a melting point of 223° C., $[\alpha]_D +128.2°$ to 132°, similar to that of the desired standard product.

Evaluation of Cells From Various Batches

Evaluation of cells of *Rhodococcus fascians* ATCC 12975 (*Nocardia salmonicolor* SC 6310) collected from various batches were carried out in a 100-mL reactor at 37° C., 250 RPM on a shaker. Cells were grown in medium 1 for 40 to 60 hours in 380-liter fermentors, harvested by Sharples Centrifuge, and cell pastes were collected. Cells were suspended in 0.2 M Tris-HCl buffer pH 6.8 and cells suspensions were supplied with 1600 μgm/ml of substrate. Transformation were conducted in 500 ml flasks as described. Periodically, samples were taken, extracted with ethyl acetate and evaluated by HPLC analysis. Results are as shown in Table 5.

Evaluation of Various Carbon Sources

Medium 1 was used to evaluate the effect of various carbon sources on the synthesis of reductase enzyme in *Rhodococcus fascians* ATCC 12975 (*Nocardia salmonicolor* SC 6310).

Medium 1 supplemented with different carbon sources (maltose, lactose, glycerol, sodium acetate, ethanol, Sucrose, sorbitol) was used in place of glucose to grow *Rhodococcus fascians* ATCC 12975 (*N. salmonicolor* SC 6310). Cells were grown in 500-ml flasks containing 100 ml of medium. A 26-hour grown culture in medium 2 was used as an inoculum. A 0.5% inoculum was used and cultures were grown at 28° C., 280 r.p.m. Cells were harvested after hours by centrifugation, and suspended in 0.2 M Tris-HCl buffer, pH 7.0, at 20% w/v cell concentration. The substrate (250 μgm/ml) was supplied to cell suspensions, and the transformation was conducted at 45° C. and 280 r.p.m. for 2 hours.

Results of the analysis indicated that the transformation of substrate to product by cell suspensions of *Rhodococcus fascians* ATCC 12975 (*N. salmonicolor*) gave higher activity with maltose, fructose, sorbitol, and glucose as carbon and energy source (Table 6).

TABLE 5

Evaluation of *Rhodococcus fascians* ATCC 12975
(*Nocardia salmonicolor* SC 6310) from various batches
to conduct the transformation to desired product [a].

| | Product Analysis (compound XA, μgm/ml) | | | | Conversion |
|---|---|---|---|---|---|
| Batch | 24 Hours | 48 Hours | 66 Hours | 115 Hours | (%) |
| HNPF XP 04051 | 411 | 1284 | 1500 | — | 94 |
| XP 040271 | 201 | 400 | 756 | 1555 | 97 |
| XP 05251 | — | 915 | 1500 | — | 94 |
| XP 05252 | 473 | 781 | 1316 | — | 82 |

[a] Cells were grown in 380-liter fermentors containing 250 liters medium 1 and cells were harvested after 44 hours. Cell-suspensions (20% w/v wet cells) in Tris-HCl buffer pH 6.8 were evaluated in 100 ml reactor volume contained in 500-ml flasks. Transformations were conducted at 37° C., 280 RPM on a shaker after supplementing with 1600 μgm/ml of substrate (compound IXA).

TABLE 6

Evaluation of Various Carbon Source on the Synthesis of
Reductase in *Rhodococcus fascians* ATCC 1297
(*Nocardia salmonicolor* SC 6310)

| Carbon Source | Product Synthesis (compound XA μgm/hour/gram dry cell weight) |
|---|---|
| 1.5% Glucose | 780 |
| 1.5% Maltose | 775 |
| 1.5% Lactose | 535 |
| 1.5% Glycerol | 300 |
| 1.5% Sodium Citrate | 435 |
| 1.5% Ethanol | 475 |
| 1.5% Fructose | 519 |
| 1.5% Sucrose | 243 |
| 1.5% Sorbitol | 494 |

(a) Cells were grown in medium 1 with the various carbon sources indicated for log 40 hours at 28° C., 280 r.p.m. Cells were harvested and suspended in 0.2M Tris-HCl, pH 7.0, at 20% w/v cell concentration. The substrate (compound IXA, 250 μgm/ml) was supplied and the transformation was conducted at 45° C., 280 r.p.m., for 2 hours. Specific activity expressed as μgm of product (compound XA) synthesized/h/g of dry cell weight.

Method III

Method III used the same substrate to make the same product as Method I.

Growth of *R. fascians* ATCC 12975 in a Fermentor

*R. fascians* ATCC 12975 culture was grown in a 380-liter fermentor containing 250 liters of medium 1. Growth consisted of inoculum development and fermentation stages.

Inoculum Development

Inoculum development consisted of F1 and F2 stages. In the F1 stage, frozen vials of *R. fascians* ATCC 12975 culture were inoculated into 100 mL of medium 2 (containing 2% glucose, 1% yeast extracts, 1% malt extracts, and 0.1% peptone). Growth was carried out in 500-mL flasks at 28° C., 280 RPM for 48 hours. In the F2 stage, 100 mL of F1 stage culture were inoculated into 1.5 liters of medium 2 in a 4-liter flask and incubated at 28° C., 180 RPM for 24 hours. A germinator containing 250 liters of medium A was inoculated with 1.5 L of F2 stage inoculum and grown for 24 hours at 28° C., 150 RPM, 200 LPM (liter per minute) aeration.

Fermentation

Fermentors containing 250 liters of medium 1 were inoculated with 13 liters of germinator-growth inoculum. Fermentations were conducted for 40 hours at 28° C., 250 RPM, and 200 LPM aeration and pH 6.8–7.0. Compound XA (5 grams in 30 mL of dimethylformamide) was added as an inducer after 22 hours of growth in a fermentor. To determine the specific activity of cells during fermentation, cells were periodically harvested by centrifugation from 200 mL of culture broth. Cell suspensions (10% w/v wet cells) were prepared in 0.1 M phosphate buffer (pH 6.8) and 250 µgm/mL of compound XA (in dimethylformamide) was added. The biotransformation was conducted in a 125-mL flask with a reaction volume of 25 mL at 37° C., 280 RPM for 2 hours. Periodically, samples were analyzed for the transformation of compound XA to compound XIA by HPLC. The specific activity was expressed as µgm of compound XIA produced/hour/gram of dry cells. After 40 hours of fermentation, cells were harvested with the aid of a Sharples centrifuge and the wet cell pastes were collected and stored at –60° C. until further use. About 8 kg of wet cell paste were collected from each fermentation.

Preparation of Cell Extracts

Cell-suspensions of *Rhodococcus fascians* ATCC 12975 (20% w/v, wet cells) in 700 mL of 0.1 M phosphate buffer (pH 6.8) were disintegrated by sonication at 4° C. Disintegrated cell-suspensions were centrifuged at 15,000×g for 15 minutes to remove cell debris. The supernatant solution in referred to as cell extracts herein.

Ammonium Sulfate Fractionation

To the cell extracts, 20 mL of protamine sulfate solution (2% solution in 0.1 M Tris-HCl) was added dropwise with continuous stirring at 4° C. After standing for 30 minutes, the extracts were centrifuged at 15,000×g for 15 minutes. The supernatant solution containing enzyme activity was fractionated by solid ammonium sulfate at 4° C. in a stepwise manner to provide 30, 50, 70 and 90% saturation. The precipitate obtained after each fractionation, e.g.,. 0–30%, 30–50%, 50–70%, and 70–90% saturation were collected by centrifugation at 15,000×g for 15 minutes, dissolved in 50 mM phosphate buffer, pH 6.8, and dialyzed at 4° C. for 16 hours in the same buffer to remove ammonium sulfate.

Transformation of Compound XA by Cell Extracts

Crude cell extracts, protamine sulfate supernatant and ammonium sulfate fractions were used to catalyze the transformation of compound XA to compound XIA at 25° C., 90 RPM after supplementing with 400 µg/mL of compound XA. Periodically, samples were taken and extracted with 2 volumes of ethyl acetate. After centrifugation, the ethyl acetate layer was collected and dried under nitrogen. Oily residue obtained was dissolved in methanol, filtered through 0.2 µm LID/X filter and analyzed by HPLC. Protein in cell fractions were determined by BioRad assays. The specific activity was defined as µmoles of compound XIA produced from compound XA per hour per mg of protein.

Method IV

Growth of *R. fascians* ATCC 12975 and the Transformation of Compound XA

Method IV used the same substrate to make the same product as Method I. *R. fascians* ATCC 12975 culture was grown in a 380-liter fermentor as described in Method III. Cells collected from the various batches were evaluated to conduct the transformation of compound XA to compound XIA. Reactions were conducted in a 500-mL flask containing 100 mL of 20% w/v cell suspensions at 37° C., 280 RPM after supplementing with 1600 µgm/mL of compound XA. After 66 to 115 hours of the transformation, a 94 to 98% conversion yield of compound XA to compound XIA was obtained. The optical purity of compound XIA was 98 to 99% as judged by the chiral HPLC.

Cells from the above batch were used to prepare the cell extract and subsequently treated with the protamine sulfate and ammonium sulfate as described above. Transformation of compound XA to compound XIA was conducted using various fractions. Results are as shown in Table 7. About 8-fold purification of enzyme which catalyzed the transformation of compound XIA was obtained.

TABLE 7

Purification of Reductase Enzyme from *R. fascians* ATCC 12975 and Conversion of Compound XA to Compound XIA

| Fraction | Activity Compound XIA (µmol/mL) | Volume (mL) | Total Activity Compound XIA (µmol) | Protein (mg/mL) | Total Protein (mg) | Specific Activity (µmol/h/mg) | Recovery (%) |
|---|---|---|---|---|---|---|---|
| Cell extracts | 66.4 | 676 | 44500 | 3.75 | 2512 | 4.380 | 100 |
| Protamine sulfate treatment | 88.3 | 500 | 44159 | 3.0 | 1500 | 7.356 | 99 |
| Ammonium sulfate treatment (0–30% suturation) | 416 | 72 | 29948 | 3.2 | 230 | 32.52 | 67.3 |

Transformation of compound XA to compound XIA by various fractions were conducted at 25 C., 90 RPM, for one hour after supplementing with 400 µg/ml of compound XA.

EXAMPLE 2

[3R-[1(S*),3α,4α]]-3-(Acetyloxy)-1,3,4,
5-tetrahydro-4-(4-methoxyphenyl)-1-
(2-pyrrolidinylmethyl)-6-(trifluoromethyl)-2H-
1-benzazepin-2-one, monohydrochloride

Method I

A. [3R-[1(S*),3α,4α]]-1-(Benzyloxycarbonyl-2-pyrrolidinyl)methyl]-3-hydroxy-1,3,4,5 -tetrahydro-4-(4-methoxyphenyl)-6-(trifluoromethyl)-2H-1-benzazepin-2-one (3R-cis)-3-Hydroxy-4-(4-methoxyphenyl)-6-(trifluoromethyl)-1,3,4,5-tetrahydro-2H-1 -benzazepin-2-one (0.8 g, 2.3 mmol) was added to a suspension of sodium hydride (0.066 g, 2.7 mmol) in dimethylformamide (23 mL). After 1 hour at room temperature, S-1-(benzyloxycarbonyl)-2-(bromoethyl)pyrrolidine (0.97 g, 3.4 mmol) was added. The reaction mixture was heated at 65° C. for 2.5 hours and then additional amounts of sodium hydride (0.028 g, 1.14 mmol) and S-1-(benzyloxycarbonyl)-2-(bromomethyl)pyrrole (0.33 g, 1.14 mmol) were added. After an additional 1 hour at 65° C., the mixture was cooled and then diluted with water and extracted with ethyl acetate three times. The ethyl acetate extracts were combined, washed with 10% aqueous lithium chloride (dried magnesium sulfate) and concentrated. The crude residue was chromatographed on a silica gel column and eluted with 20–40% ethyl acetate in hexane to obtain the title compound (0.8 g).

B. [3R-[1(S*),3α,4α]]-3-Acetoxy-1-(1-benzyloxycarbonyl-2-pyrrolidinyl)methyl]- 1,3,4,5tetrahydro-4-(4-methoxyphenyl)-6-(trifluoromethyl)-2H-1-benzazepin-2-one N,N-Dimethylaminopyridine (0.45 g/3.7 mmol) was added to a solution of [3R-[1(S*),3α,4α]]-1-(benzyloxycarbonyl-2-pyrrolidinyl)methyl]-3 -hydroxy-1,3,4,5-tetrahydro-4-(4-methoxyphenyl)-6-(trifluoromethyl)-2H-1-benzazepin-2-one (1.14 g, 1.85 mmol) and acetic anhydride (0.87 mL, 0.24 mmol) in dichloromethane (20 mL). The mixture was stirred at room temperature for 4 days, absorbed into silica gel (60 mesh) and flash chromatography on a silica gel column. Elution with 10–40% ethyl acetate in hexane afforded the title compound (0.68 g) as a viscous oil.

C. [3R-[1(S*),3α,4α]]-3-(Acetyloxy)-1,3,4,5-tetrahydro-4-(4-methoxyphenyl)-1 -(2-pyrrolidinylmethyl)-6-(trifluoromethyl)-2H-1-benzazepin-2-one, monohydrochloride Ammonium formate (0.23 g, 3.64 mmol) was added in one portion to a suspension of 10% palladium on charcoal (0.05 g, and [3R-1(S*),3α,4α]]-3-acetoxy-1-(1 -benzyloxycarbonyl-2-pyrrolidinyl)methyl]-1,3,4,5-tetrahydro-4-(4-methoxyphenyl)-6-(trifluoromethyl)-2 H-1-benzazepine-2-one (0.48 g, 0.73 mmol) in methanol (10 mL). The mixture was heated under reflux for 30 minutes, whereupon it was cooled and filtered through Celite. The residual solids were washed with ethyl acetate. The filtrate was concentrated to obtain a white foam, which was dissolved in ether and treated with excess etheral hydrogen chloride solution. The solution was concentrated and crystallized from toluene/hexane to obtain the title compound (0.325 g) as an off-white solid, melting point 217° to 219° C. [α]$_D$=+78.7° (c=1.0, methanol).

Analysis for $C_{25}H_{27}F_3N_2O_4$·HCL·0.29$H_2O$: Calc'd: C 58.06; H 5.37; N 5.42; C16.96; F 11.02; Found: C 58.37; H 5.57; N 5.54; C17.05; F 10.58.

Method II

A. 1-[(Phenylmethoxy)carbonyl]-L-proline

CBZCl (1300 mL) and a solution of NaOH (346.5 g) in $H_2O$ (1700 mL) were added dropwise to a 0° C. solution of L-proline (1000 g) and NaOH (346.5 g) on $H_2O$ (3500 mL) at such a rate as to keep the reaction temperature between 1° and 3° C. Initial pH of the L-proline/NaOH solution was pH 11.5. CBZCl was added until the pH dropped to 9. Both CBZCl and the NaOH solution were then added simultaneously keeping the pH between 9–10. The remainder of the NaOH solution was then added to give a final pH of 11.5.

After being stirred at 1° C. for 1 hour, the pH of the solution was adjusted to pH 2 with concentrated HCl. During this time, the reaction temperature increased to 11.5° C., and an oil separated.

The mixture was extracted with ethyl acetate (2×4000 mL). The combined organic extracts were extracted with brine (2×1000 mL), dried ($Na_2SO_4$), filtered, and concentrated in vacuo to a syrup.

After concentrating the Z-proline to a syrup (approx. 2500 mL), an equal volume of toluene (2500 mL) and a seed crystal were added. With stirring, small portion of hexane were added over the course of two hours (total of 5000 mL). The mixture was then stirred for three hours and filtered. Yield: 2108 g, (98%), melting point 72° to 73° C. If the addition is too rapid, the product will gum out prior to crystallization.) TLC: $CH_2Cl_2$-methanol (MeOH) (9:1).

B. 1-[(Phenylmethoxy)carbonyl]-L-proline, methyl ester

Trimethylsilyl chloride (211 mL) was added to a solution of compound A (2108 g) in methanol (15 L) containing $HC(OCH_3)_3$ (2108 mL). After stirring for 24 hours, toluene (4000 mL) was added and the solution concentrated in vacuo to a syrup. After dilution with ethyl acetate (8000 mL), the solution was extracted with water (1×3000 mL, pH of the aqueous phase after extraction with pH 5) and brine (1×2000 mL), then dried (MgSO$_4$), filtered and concentrated to a syrup (2269 g, 102%) which was used "as is" in the next reaction.

TLC: $CH_2Cl_1$-MeOH (95:5) $R_f$=0.9 (ceric sulfate/ammonium molybdate) ethyl acetate (EtOAc)-Hexane (1:1) $R_f$=0.9.

C. (S)-2-(Hydroxymethyl)-1-pyrrolidinecarboxylic acid, phenylmethyl ester

NaBH$_4$ (418.5 g) was added to a solution of compound B (1134.5 g) in t-butanol (4700 mL) at ambient temperature. After heating to 45° C., bath temperature 50° C.), methanol (1145 mL) was added dropwise over the course of two hours. Dropwise methanol addition was started at 45° C. After twenty minutes (600 mL added), the temperature had increased to 50° C. The bath was removed and the methanol addition was then stopped. The internal temperature increased to 55° C. When the temperature started to decrease, the methanol addition was resumed and the internal temperature maintained around 52° C. using external heat when necessary. Total time for the methanol addition was two hours.

Vigorous hydrogen evolution increased during the addition of methanol. After the addition was complete, hydrogen evolution continued strongly for about one hour before it started to taper-off to a slow evolution. The reaction was then stirred at 50° C. for an additional ninety minutes.

The reaction was allowed to cool to 25° C. and water (9500 mL) was added slowly. The mixture was stirred for thirty minutes (to dissolve the solids). After concentrating in vacuo to approximately 6000 mL, brine (2000 mL) was added and the mixture extracted with ethyl acetate (2×4000 mL). The combined organic extracts were extracted with acidic brine (0.5% HCl in brine, 1×2000 mL), brine (3×1000 mL), dried (MgSO$_4$), filtered, concentrated to a cloudy syrup, and then co-evaporated with toluene (3×1000 mL). The resulting syrup was dried under high Vacuum for 18 hours to afford 910 g (90% yield) of compound C.

TLC: ethyl acetate-hexanes (1:1) R$_f$=0.35 ( ceric sulfate/ammonium molybdate) shows the alcohol (major) along with the starting ester (estimated at 5% or less).

D. (S)-2-[[[(4-Methylphenyl)sulfonyl]oxy]-methyl]-1-pyrrolidinecarboxylic acid, phenylmethyl ester Tosyl chloride (1920 g) was added to a chilled (10° C.) solution of the Z-prolinol from part C (1820 g) and dimethylaminopyridine (47.5 g) in pyridine (9500 ml). After stirring at room temperature for 18 hours, water (30 mL) was added and the solution stirred for an additional 4 hours before being concentrated in vacuo to a syrup. Ethyl acetate (8000 mL) was added and the solution extracted with 5% HCl until the aqueous phase remained acidic (2×2000 mL, aqueous phase remained acidic after the second extraction). The organic phase was then extracted with saturated NaHCO$_3$ (2×2000 mL), water (1×2000 mL), and finally with brine (1×2000 mL). The organic phase was dried (MgSO$_4$), filtered, and concentrated in vacuo to a syrup. The syrup was seeded, hexane (8000 mL) was added, and the mixture stirred at medium speed using an overhead stirrer. After two hours, the syrup started to form a semi-solid. After three hours, the mixture became the consistency of a "cheese curd", then thinned out of a fine solid. The stirring was increased and the mixture stirred overnight. The solid was collected by filtration on an 18" LAPP filter, then washed with additional hexane (3×2000 mL) to afford 2725 g of compound D. Melting point 51° to 52° C.

TLC: Ethyl acetate-hexane (1:1) R$_f$=0.7 ( ceric sulfate/ammonium molybdate).

E. [3R-[1(S*),3α,4α]]-1,3,4,5-Tetrahydro-3-hydroxy-4-(4-methoxyphenyl)-1 -[[1-[(phenylmethoxy)carbonyl]-2-pyrrolidinyl]methyl-6-trifluoromethyl)-2H-1-benzazepin-2-one Cesium carbonate (347.5 g) was added to a solution of (3R-cis)-1,3,4,5-tetrahydro-3-hydroxy-4-(4-methoxyphenyl)-6-(trifluoromethyl)-2H-1 -benzazepin-2-one and compound D (347.9 g) in dimethylformamide (2030 mL, sieve dried) under nitrogen. The mixture was then heated at 50° C. for twenty-four hours. The reaction mixture was cooled to room temperature, diluted with ethyl acetate (2030 mL), and filtered through Celite®. The Celite bed was washed with additional ethyl acetate (3×500 mL). The filtrate was concentrated in vacuo to a dense oil. The oil was dissolved in ethyl acetate (4 liters) then washed sequentially with 10% hydrochloric acid (2×500 mL), distilled water (2×500 mL), and brine (2×750 mL). The organic phase was dried over anhydrous magnesium sulfate, filtered and then concentrated in vacuo to a semi-solid. The residue was triturated with diethyl ether (400 mL) to form a free-flowing solid and then stored at 4° C. overnight. The solid was collected by filtration and washed with additional cold (4° C.) diethyl ether (2×200 mL). The white powder was dried under vacuum overnight to yield 374 g of compound E. Melting point=181° C.; [α]$_D$=+145° C. (c=1, methanol).

TLC: EtOAc/Hexane (1:1), R$_f$=0.55; ceric sulfate

F. [3R-[1(S*),3α,4α]]-3-(Acetyloxy)-1,3,4,5-tetrahydro-4-(4-methoxyphenyl)-1 -(2-pyrrolidinylmethyl)-6-(trifluoromethyl)-2H-1-benzazepin-2-one, monohydrochloride Compound E (240 g) was slurried in pyridine (400 mL) under nitrogen, then treated with acetic anhydride (115 mL). The mixture was heated at 70° C. for four hours. The reaction mixture was chilled to 0° C. then treated dropwise with methanol (150 mL) at a rate to maintain the temperature below 30° C. The reaction mixture was then stirred at about 30° C. for thirty minutes. Toluene (200 mL) was added and the mixture concentrated in vacuo to a thin syrup. The syrup was coevaporated four times with solutions of toluene/methanol (1:1, 4×500 mL).

The resulting syrup was dissolved in ethyl acetate (1500 mL) then washed sequentially with 10% hydrochloric acid (2×200 mL), distilled water (2×200 mL), saturated sodium bicarbonate (3×200 mL), distilled water (2×200 mL), and brine (2×200 mL). The organic layer was dried over anhydrous magnesium sulfate, filtered, then concentrated in vacuo to a thin syrup, which was used "as is" in the next reaction. The syrup was dissolved in ethyl acetate (1200 mL), treated with acidic acid (96 mL), then purged with nitrogen for ten minutes via a gas dispersion tube. Pd(OH)$_2$/C (12 g) was added, and the mixture was hydrogenated at atmospheric pressure for two hours with vigorous stirring. After purging with nitrogen, the suspension was filtered through Celite and the bed washed with additional ethyl acetate (3×300 mL). The filtrate was concentrated in vacuo, then coevaporated with toluene (3×500 mL). The residual syrup was dissolved in ethyl acetate (1500 mL). Saturated sodium bicarbonate solution was added at pH 7.2 to raise the pH to 8.9. The ethyl acetate layer was separated and the aqueous phase reextracted with ethyl acetate (2×1000 mL). The combined ethyl acetate layers were washed sequentially with saturated sodium bicarbonate (2×500 mL), distilled water (2×500 mL), and brine (2×500 mL). The ethyl acetate solution was dried over anhydrous magnesium sulfate and filtered. 1 M HCl in ethyl acetate (570 mL) was added with stirring to the filtrate, and the solution was concentrated in vacuo to a thin syrup. The syrup was diluted with ethyl acetate to about 750 mL total volume, seeded, then left standing at room temperature overnight. The solid precipitate was collected by filtration, then washed with cold (4° C.) ethyl acetate (2×100 mL) and diethyl ether (2×200 mL). The white crystalline solid was dried under vacuum overnight to yield 201 g of the product. The material was combined with a second batch obtained from a 60 g input of compound E. HI=99.6; melting point 223° to 225° C.

TLC: CH$_2$Cl$_2$/MeOH (9:1), R$_f$=0.3, ceric sulfate; [α]$_D$=+80.7 (c=1,MeOH).

EXAMPLE 3

[3R-[1(S*),3α,4α]]-1,3,4,5-tetrahydro-3-hydroxy-4-(4-methoxyphenyl)-1-( 2-pyrrolidinylmethyl)-6-(trifluoromethyl)-2H-1-benzazepin-2-one, monohydrochloride A suspension of 20% Pd(OH)$_2$/C (10 g) in ethyl acetate (1800 mL)/acetic acid (600 mL) containing compound A from Example 2, Method II (200 g) was purged with nitrogen for ten minutes via a gas dispersion tube, then hydrogenated at atmospheric pressure for three hours. The slurry was purged with nitrogen for ten minutes and then filtered through Celite. The bed was washed with additional ethyl acetate (3×200 mL). The filtrate was concentrated in vacuo and then coevaporated with toluene (4×500 mL). The residue was dissolved in ethyl acetate (200 mL) and then treated slowly with saturated sodium bicarbonate solution (1000 mL). The mixture was treated with saturated sodium bicarbonate solution to pH 9.

After the addition of saturated brine (400 mL), the organic layer was separated and the aqueous layer reextracted with ethyl acetate (2×400 mL). The combined organic layers were washed with saturated brine (5×1000 mL) until the aqueous layer was neutral. The organic phase was dried over anhydrous magnesium sulfate for fifteen minutes. The addition of anhydrous magnesium sulfate resulted in significant exotherm (about 35° C.) which indicated the solution contained excessive amounts of water. During the drying process it also became obvious that product was precipitating from the solution. The mixture was filtered. The cake was washed thoroughly with dichloromethane to dissolve the precipitated product. The combined filtrates were concentrated in vacuo. The solid residue was slurried in ethyl acetate (3000 mL) then treated with 1.5 M HCl in ethyl acetate (280 mL) over the course of five minutes. The mixture was stirred for sixty minutes then filtered. The solid was washed with additional ethyl acetate (2×200 mL) and diethyl ether (2×300 mL). The solid was dried under vacuum for five days. This was required to remove residual HCl. The vacuum was interrupted occasionally to facilitate removal of the HCl vapors. A total of 138 g of the product was obtained. HI 99.5; melting point 163° to 167° C.; $[\alpha]_D = +75.1°$ (c=1 MeOH)

TLC: $CH_2Cl_2/MeOH$ (9:1); $R_f = 0.2$.

What is claimed is:

1. A process for transforming a substrate having the formula

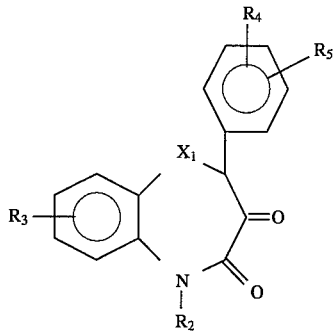

to a product having the formula

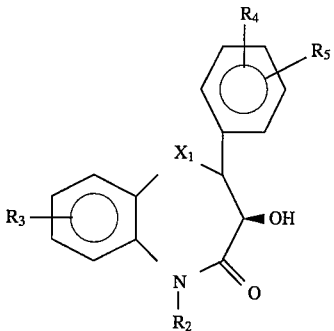

wherein:

$X_1$ is $-CH_2-$ or $-S-$;

when $X_1$ is $-CH_2-$, $R_2$ is hydrogen,

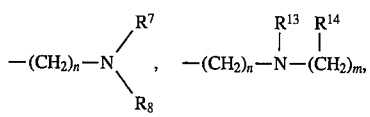

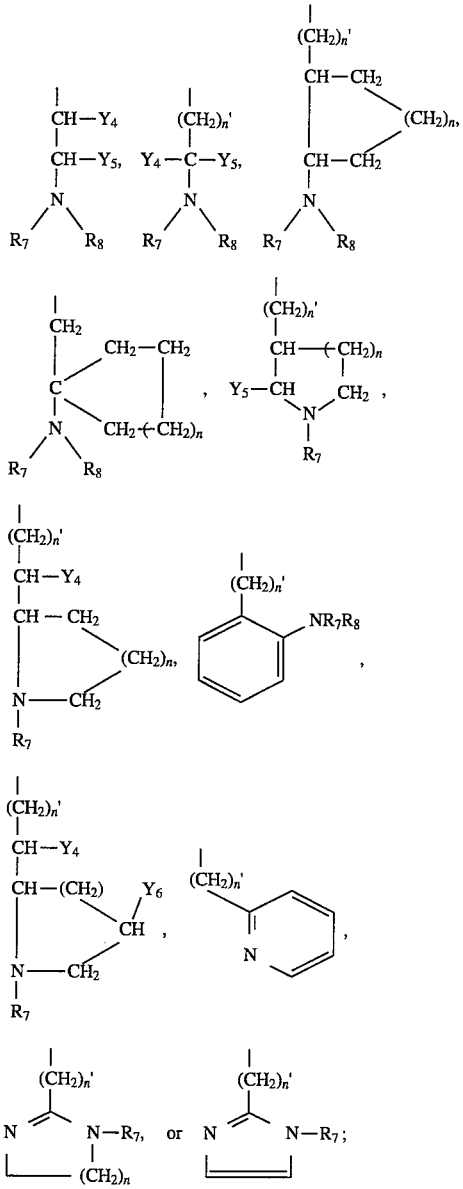

when $X_1$ is $-S-$, $R_2$ is hydrogen,

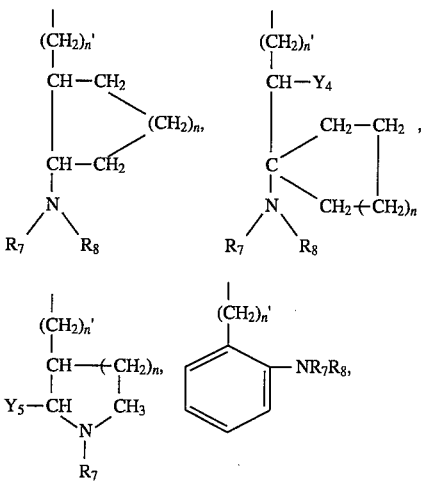

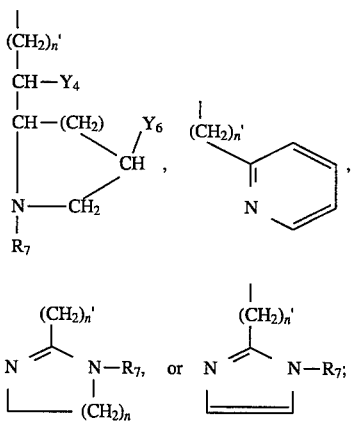

$R_3$, $R_4$ and $R_5$ are each independently hydrogen, halogen, alkyl, alkoxy, aryloxy, arylalkoxy, diarylalkoxy, arylalkyl, cyano, hydroxy, alkanoyloxy, nitro,

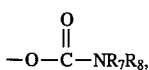

fluoro-substituted alkoxy, fluro-substituted alkyl, (cycloalkyl)alkoxy,

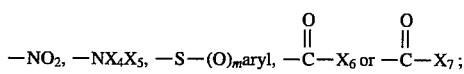

$R_7$ and $R_8$ are each independently hydrogen, alkyl, cycloalkyl, or arylalkyl; or $R_7$ and $R_8$, together with the nitrogen atom to which they are attached, are azetidinyl, pyrrolidinyl, piperidinyl, or morpholinyl;

$R_{13}$ is hydrogen, alkyl, cycloalkyl, or arylalkyl;

$R_{14}$ is heterocyclo or heteroaryl;

$X_4$ and $X_5$ are each independently hydrogen, alkyl, alkanoyl, arylcarbonyl, heteroarylcarbonyl, or $-C-NR_7R_8$;

$X_6$ is hydroxy, alkoxy, aryloxy, amino, alkylamino or dialkylamino;

$X_7$ is alkyl, alkoxy, or aryloxy;

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ is hydrogen, hydroxy, alkoxy, aryloxy or aralkoxy;

m is 0, 1, or 2; and n or n' is 0, 1, 2, or 3;

and wherein the process comprises treating the substrate with a reductase or a reductase-supplying microorganism.

2. The process of claim 1:
(a) further comprising culturing the reductase-supplying microorganism; and
(b) wherein the treatment of the substrate is carried out by adding the substrate to the reductase-supplying microorganism during the culturing step.

3. The process of claim 2, wherein the culturing step is carried out by placing the microorganism in a medium comprising a carbon source, a nitrogen source, and mineral salts.

4. The process of claim 1, further comprising:

(a) culturing the reductase-supplying microorganism prior to treating the substrate; and
(b) suspending the cultured reductase-supplying microorganism in a buffered solution;

and wherein the treatment of the substrate is carried out by adding the substrate to the cell-suspensions of microorganisms.

5. The process of claim 4, wherein the culturing step is carried out by placing the microorganism in a medium comprising a carbon source, a nitrogen source, and mineral salts.

6. The process of claim 3, wherein the buffered solution has a pH of about 6.8 to 7.0.

7. The process of claim 1, wherein the reductase-supplying microorganism is selected from a group consisting of Achromobacter, Acinetobacter, Actinomyces, Alcaligenes, Arthrobacter, Azotobacter, Bacillus, Brevibacterium, Corynebacterium, Flavobacterium, Methylomonas, Mycobacterium, Nocardia, Pseudomonas, Rhodococcus, Streptomyces, Xanthomonas, Aspergillus, Candida, Fusarium, Geotrichum, Hansenula, Kloeckera, Penicillium, Pichia, Rhizopus, Rhodotorula, Saccharomyces, Trichoderma, and Rhodopseudomonas.

8. The process of claim 1, wherein $R_2$ is hydrogen.

9. The process of claim 1, wherein $R_3$ is trifluoromethyl.

10. The process of claim 1, wherein one of $R_4$ and $R_5$ is alkoxy and the other is hydrogen.

11. The process of claim 1, wherein the substrate has a concentration of about 0.1 to 5.0 percent.

12. The process of claim 1, further comprising adding an additional amount of the substrate subsequent to treating the substrate with the reductase or the reductase-supplying microorganism.

13. The process of claim 1, further comprising maintaining a reaction pH between or equal to about 4 to 9.

14. The process of claim 1, further comprising maintaining a reaction temperature between or equal to about 20° C. to 60° C.

15. The process of claim 1, further comprising placing the substrate and the reductase-supplying microorganism in a fermentor and agitating and aerating the fermentor.

16. The process of claim 15, wherein the fermentor is agitated or rotated at a speed from about 50 to 1000 r.p.m.

17. The process of claim 15, wherein the fermentor is aerated at about 1 to 5 volumes of air per volume of media per minute.

18. A process for transforming a substrate having the formula

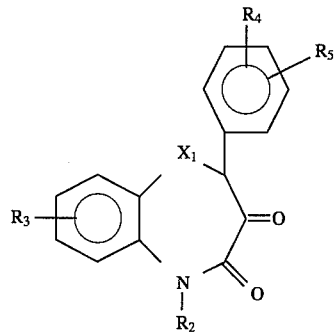

to a product having the formula

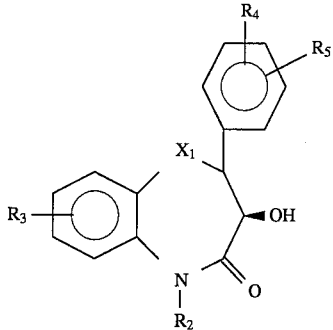

wherein:

$X_1$ is —$CH_2$— or —S—;

when $X_1$ is —$CH_2$—, $R_2$ is hydrogen,

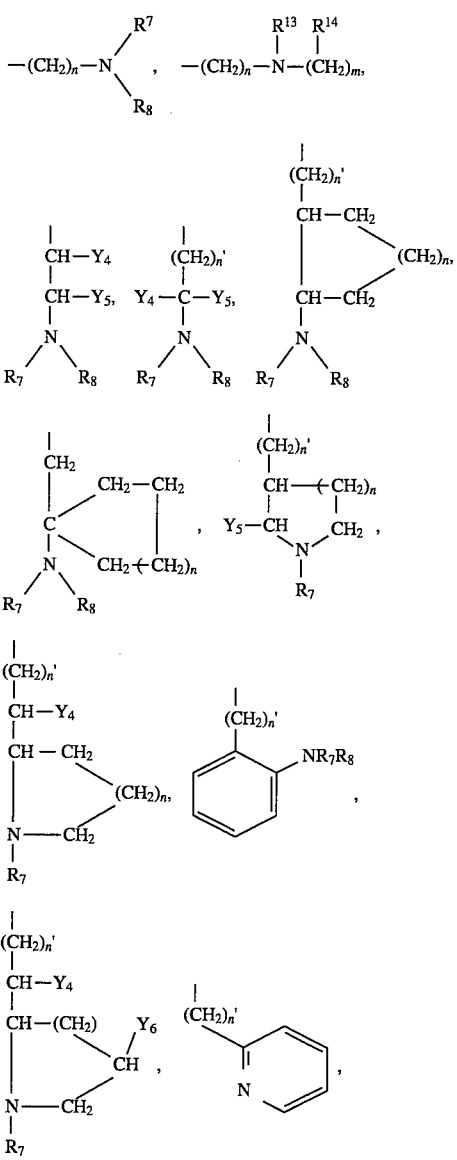

when $X_1$ is —S—, $R_2$ is hydrogen, $R_3$, $R_4$ and $R_5$ are each independently hydrogen, halogen, alkyl, alkoxy, aryloxy, arylalkoxy, diarylalkoxy, arylalkyl, cyano, hydroxy, alkanoyloxy, nitro, $$-O-\overset{O}{\underset{\|}{C}}-NR_7R_8,$$

fluoro-substituted alkoxy, fluoro-substituted alkyl, (cycloalkyl)alkoxy, $$-NO_2, -NX_4X_5, -S-(O)_m aryl, -\overset{O}{\underset{\|}{C}}-X_6 \text{ or } -\overset{O}{\underset{\|}{C}}-X_7;$$

$R_7$ and $R_8$ are each independently hydrogen, alkyl, cycloalkyl, or arylalkyl; or $R_7$ and $R_8$, together with the nitrogen atom to which they are attached, are azetidinyl, pyrrolidinyl, piperidinyl, or morpholinyl;

$R_{13}$ is hydrogen, alkyl, cycloalkyl, or arylalkyl;

$R_{14}$ is heterocyclo or heteroaryl;

$X_4$ and $X_5$ are each independently hydrogen, alkyl, alkanoyl, arylcarbonyl, heteroarylcarbonyl, or —C—$NR_7R_8$;

$X_6$ is hydroxy, alkoxy, aryloxy, amino, alkylamino or dialkylamino;

$X_7$ is alkyl, alkoxy, or aryloxy;

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ is hydrogen, hydroxy, alkoxy, aryloxy or aralkoxy;

m is 0, 1, or 2; and n or n' is 0, 1, 2, or 3;

and wherein the process comprises treating the substrate with a reductase derived from or a reductase-supplying microorganism selected from:

*Pseudomonas aeruginosa* ATCC 25619;
*Pseudomonas putida* ATCC 23973;
*Pseudomonas oleovorans* ATCC 23947;
*Acinetobacter calcoaceticus* ATCC 33305;
*Arthrobacter simplex* ATCC 6949;
*Rhodococcus fascians* ATCC 12975;
*Alkaligenes eutrophus* ATCC 17697;
*Mycobacterium vacca* ATCC 29678;
*Rhodococcus rhodochrous* ATCC 29670;
*Rhodococcus rhodochrous* ATCC 15592;
*Rhodococcus rhodochrous* ATCC 15906;
*Rhodococcus rhodochrous* ATCC 14349;
*Rhodococcus rhodochrous* ATCC 13808;
*Rhodococcus rhodochrous* ATCC 999;
*Rhodococcus rhodochrous* ATCC 29675;
*Rhodococcus rhodochrous* ATCC 21243;
*Rhodococcus rhodochrous* ATCC 19150;
*Rhodococcus rhodochrous* ATCC 29670;
*Hansenula polymorpha* ATCC 26012;
*Saccaromyces cerevisiae* ATCC 12341;
*Pichia pastoris* ATCC 28485;
*Candida rugosa* ATCC 10571; and
*Candida utilis* ATCC 26387.

19. The process of claim 18, wherein the reductase-supplying microorganism is *Rhodococcus fascians* ATCC 12975.

20. A process for transforming a substrate having the formula

[structure with $R_3$, $R_4$, $R_5$, $X_1$, N—$R_2$, =O]

to a product having the formula

[structure with $R_3$, $R_4$, $R_5$, $X_1$, OH, N—$R_2$, =O]

wherein:

$X_1$ is —$CH_2$— or —S—;

when $X_1$ is —$CH_2$—, $R_2$ is hydrogen, $$-(CH_2)_n-N\begin{array}{c}R^7\\R_8\end{array}, \quad -(CH_2)_n-N\begin{array}{c}R^{13}\ R^{14}\\|\ \ |\end{array}-(CH_2)_m,$$

[various cyclic amine structures with $CH-Y_4$, $CH-Y_5$, $(CH_2)_{n'}$, $Y_4-C-Y_5$, $CH-CH_2$, $(CH_2)_n$, $R_7$, $R_8$]

[structures with $CH_2$, $CH_2-CH_2$, C, N, $R_7$, $R_8$; and $(CH_2)_{n'}$, $CH-(CH_2)_n$, $Y_5-CH$, $CH_2$, N, $R_7$]

[structures with $(CH_2)_{n'}$, $CH-Y_4$, $CH-CH_2$, $(CH_2)_n$, N—$CH_2$, $R_7$; and $(CH_2)_{n'}$, $NR_7R_8$ on benzene ring]

[structures with $(CH_2)_{n'}$, $CH-Y_4$, $CH-(CH_2)$, $Y_6$, CH, N—$CH_2$, $R_7$; and $(CH_2)_{n'}$ on pyridine ring]

-continued

[structures: (CH2)n'-N=... N-R7, or (CH2)n'-N=... N-R7;]

when $X_1$ is —S—, $R_2$ is hydrogen,

[structures with (CH2)n', CH—CH2, CH—CH2, (CH2)n, N, R7, R8; and CH—Y4, CH2—CH2, C, CH2(CH2)n, N, R7, R8;]

[structures with (CH2)n', CH—(CH2)n, Y5—CH, CH3, N, R7; and (CH2)n'-phenyl-NR7R8,]

[structures with (CH2)n', CH—Y4, CH—(CH2), Y6, CH, N—CH2, R7; and (CH2)n'-pyridyl,]

[structures: (CH2)n'-N=... N-R7, or (CH2)n'-N=... N-R7;]

$R_3$, $R_4$ and $R_5$ are each independently hydrogen, halogen, alkyl, alkoxy, aryloxy, arylalkoxy, diarylalkoxy, arylalkyl, cyano, hydroxy, alkanoyloxy, nitro, $$-O-\overset{O}{\underset{\|}{C}}-NR_7R_8,$$

fluoro-substituted alkoxy, fluoro-substituted alkyl, (cycloalkyl)alkoxy, $$-NO_2, -NX_4X_5, -S-(O)_m\text{aryl}, -\overset{O}{\underset{\|}{C}}-X_6 \text{ or } -\overset{O}{\underset{\|}{C}}-X_7;$$

$R_7$ and $R_8$ are each independently hydrogen, alkyl, cycloalkyl, or arylalkyl; or $R_7$ and $R_8$, together with the nitrogen atom to which they are attached, are azetidinyl, pyrrolidinyl, piperidinyl, or morpholinyl;

$R_{13}$ is hydrogen, alkyl, cycloalkyl, or arylalkyl;

$R_{14}$ is heterocyclo or heteroaryl;

$X_4$ and $X_5$ are each independently hydrogen, alkyl, alkanoyl, arylcarbonyl, heteroarylcarbonyl, or —C—NR7R8;

$X_6$ is hydroxy, alkoxy, aryloxy, amino, alkylamino or dialkylamino;

$X_7$ is alkyl, alkoxy, or aryloxy;

$Y_4$ and $Y_5$ are each independently hydrogen, alkyl, aryl or arylalkyl, provided that when both are present they are not both hydrogen, and provided further that when both are attached to the same carbon atom neither of them is hydrogen;

$Y_6$ is hydrogen, hydroxy, alkoxy, aryloxy or aralkoxy;

m is 0, 1, or 2; and n is n' is 0, 1, 2, or 3;

and wherein the process comprises treating the substrate with a reductase derived from or a reductase-supplying microorganism selected from:

*Pseudomonas aeruginosa;*

*Pseudomonas putida;*

*Pseudomonas oleovorans;*

*Acinetobacter calcoaceticus;*

*Arthrobacter simplex;*

*Rhodococcus fascians;*

*Nocardia salmonicolor;*

*Alkaligenes eutrophus;*

*Mycobacterium bacca;*

*Rhodococcus rhodochrous;*

*Hansenula polymoropha;*

*Saccaromyces cerevisiae;*

*Pichia pastoris;*

*Candida rugosa;* and

*Candida utilis.*

21. The process of claims 1, 2, 4, 7, 19, 9, 10, 3, 5, 11, 12, 13, 6, 14, 15, 16, 17, or 20:

(a) wherein $R_2$ of the substrate is hydrogen;

(b) wherein $X_1$ of the substrate is —CH2—; and (c) further comprising reacting the substrate with a compound of the formula

[structure: cyclopentane with L and NH substituents]

wherein L is a leaving group) to form the product having the structure

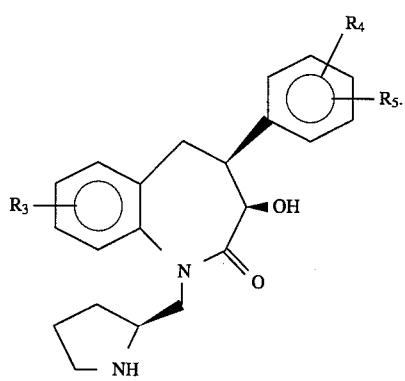
22. The process of claim 21, wherein $R_3$ is trifluoromethyl and one of $R_4$ and $R_5$ is methoxy and the other is hydrogen.
23. The process of claim 21, further comprising acylating either the substrate or the product of claim 21 to form a new compound of the formula
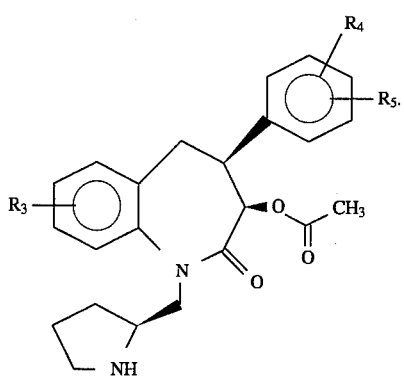
24. The process of claim 23, wherein $R_3$ is trifluoromethyl and one of $R_4$ and $R_5$ is methoxy and the other is hydrogen.
* * * * *